US011344739B2

(12) United States Patent
Sharma

(10) Patent No.: US 11,344,739 B2
(45) Date of Patent: May 31, 2022

(54) SYSTEM AND METHODS FOR TREATING CANCER CELLS WITH ALTERNATING POLARITY MAGNETIC FIELDS

(71) Applicant: Vivek K. Sharma, San Ramon, CA (US)

(72) Inventor: Vivek K. Sharma, San Ramon, CA (US)

(73) Assignee: ASHA MEDICAL, INC., San Ramon, CA (US)

( * ) Notice: Subject to any disclaimer, the term of this patent is extended or adjusted under 35 U.S.C. 154(b) by 0 days.

(21) Appl. No.: 17/308,019

(22) Filed: May 4, 2021

(65) Prior Publication Data

US 2021/0251850 A1 Aug. 19, 2021

Related U.S. Application Data

(63) Continuation of application No. 16/784,239, filed on Feb. 6, 2020, now Pat. No. 11,027,143.

(Continued)

(51) Int. Cl.
*A61N 2/06* (2006.01)
*A61N 2/02* (2006.01)
*A61N 2/00* (2006.01)
*A61K 45/06* (2006.01)
*A61J 1/20* (2006.01)
*A61M 5/19* (2006.01)
(Continued)

(52) U.S. Cl.
CPC ............ *A61N 2/004* (2013.01); *A61J 1/2006* (2015.05); *A61J 1/2037* (2015.05); *A61J 1/2072* (2015.05); *A61K 45/06* (2013.01); *A61M 5/19* (2013.01); *A61M 39/14* (2013.01); *A61M 39/24* (2013.01); *A61N 2/002* (2013.01); *A61N 2/02* (2013.01); *A61B 5/055* (2013.01); *A61B 6/032* (2013.01); *A61B 6/037* (2013.01); *A61B 6/50* (2013.01); *A61N 2/06* (2013.01)

(58) Field of Classification Search
CPC ........ A61N 2/00–12; A61N 5/10–1084; A61N 2005/1085–1098
See application file for complete search history.

(56) References Cited

U.S. PATENT DOCUMENTS 3,756,390 A 9/1973 Abbey et al.
4,781,679 A 11/1988 Larkin
(Continued)

FOREIGN PATENT DOCUMENTS

AU 2019200616 B2 2/2019
CA 3129257 A1 8/2020
(Continued)

OTHER PUBLICATIONS

International Search Report and Written Opinion dated Sep. 27, 2019, International Application No. PCT/US2019/040882 filed Jul. 9, 2018.
(Continued)

*Primary Examiner* — Thaddeus B Cox
(74) *Attorney, Agent, or Firm* — Timothy L. Scott

(57) ABSTRACT

Systems and method for destroying or inhibiting cancer cells and other rapidly-dividing cells include applying AP magnetic fields having a frequency of 0.5-500 kHz and a field strength of 0.5-5 mT to a target body area that includes the cancer or other rapidly-dividing cells.

20 Claims, 8 Drawing Sheets

Related U.S. Application Data

(60) Provisional application No. 62/802,685, filed on Feb. 7, 2019.

(51) Int. Cl.
*A61M 39/14* (2006.01)
*A61M 39/24* (2006.01)
*A61B 5/055* (2006.01)
*A61B 6/03* (2006.01)
*A61B 6/00* (2006.01)

(56) References Cited

U.S. PATENT DOCUMENTS

| | | |
|---|---|---|
| 5,114,411 A | 5/1992 | Haber et al. |
| 5,637,087 A | 6/1997 | O'Neil et al. |
| 6,679,827 B2 | 1/2004 | Sandstrom |
| 6,868,289 B2 | 3/2005 | Palti |
| 6,926,659 B1 | 8/2005 | Sandstrom |
| 6,960,184 B2 | 11/2005 | Willis et al. |
| 7,016,725 B2 | 3/2006 | Palti |
| 7,104,971 B2 | 9/2006 | Hjertman |
| 7,519,411 B2 | 4/2009 | Long |
| 7,890,183 B2 | 2/2011 | Palti et al. |
| 8,005,528 B2 | 8/2011 | Long |
| 8,019,414 B2 | 9/2011 | Palti |
| 8,129,694 B2 | 3/2012 | Balakin |
| 8,175,698 B2 | 5/2012 | Palti et al. |
| 8,178,859 B2 | 5/2012 | Balakin |
| 8,188,688 B2 | 5/2012 | Balakin |
| 8,373,145 B2 | 2/2013 | Balakin |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,614,554 B2 | 12/2013 | Balakin |
| 8,637,818 B2 | 1/2014 | Balakin |
| 8,684,901 B1 | 4/2014 | Zabara |
| 8,690,419 B2 | 4/2014 | Faccioli et al. |
| 8,706,258 B2 | 4/2014 | Nabors, Sr. et al. |
| 8,706,261 B2 | 4/2014 | Palti |
| 8,710,462 B2 | 4/2014 | Balakin |
| 8,957,396 B2 | 2/2015 | Balakin |
| 8,965,527 B2 | 2/2015 | Ruse et al. |
| 8,992,990 B2 | 3/2015 | Hua et al. |
| 9,018,601 B2 | 4/2015 | Balakin |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,081,878 B2 | 7/2015 | Rofougaran |
| 9,095,270 B2 | 8/2015 | Flynn |
| 9,157,840 B2 | 10/2015 | Cho et al. |
| 9,199,043 B2 | 12/2015 | Chattaraj et al. |
| 9,314,649 B2 | 4/2016 | Balakin |
| 9,440,068 B2 | 9/2016 | Palti et al. |
| 9,486,512 B2 | 11/2016 | Kim et al. |
| 9,486,625 B2 | 11/2016 | Crawford et al. |
| 9,636,495 B2 | 5/2017 | Szasz et al. |
| 9,655,669 B2 | 5/2017 | Palti et al. |
| 9,682,247 B2 | 6/2017 | Susedik et al. |
| 9,687,668 B2 | 6/2017 | McKenna et al. |
| 9,726,647 B2 | 8/2017 | Walker et al. |
| 9,750,934 B2 | 9/2017 | Palti et al. |
| 9,757,582 B2 | 9/2017 | Sandstrom |
| 9,757,594 B2 | 9/2017 | Balakin |
| 9,777,265 B2 | 10/2017 | Subramaniam et al. |
| 9,783,808 B2 | 10/2017 | Lee et al. |
| 9,789,328 B2 | 10/2017 | Sandstrom |
| 9,809,810 B2 | 11/2017 | Subramaniam et al. |
| 9,833,617 B2 | 12/2017 | Travers et al. |
| 9,885,031 B2 | 2/2018 | Subramaniam et al. |
| 9,999,779 B2 | 6/2018 | Dougherty et al. |
| 10,030,039 B2 | 7/2018 | Ishikawa et al. |
| 10,045,910 B2 | 8/2018 | Mueller et al. |
| 10,105,491 B2 | 10/2018 | Gelblum et al. |
| 10,124,186 B2 | 11/2018 | McKenna et al. |
| 10,161,939 B2 | 12/2018 | Rao et al. |
| 10,864,139 B2 | 12/2020 | Genosar |
| 2001/0044643 A1 | 11/2001 | Litovitz |
| 2004/0267201 A1 | 12/2004 | Agerup |
| 2005/0090732 A1 | 4/2005 | Ivokov et al. |
| 2005/0209642 A1 | 9/2005 | Palti |
| 2006/0142748 A1 | 6/2006 | Foreman et al. |
| 2007/0129673 A1 | 6/2007 | Bassarab et al. |
| 2008/0171971 A1 | 7/2008 | Di Perna et al. |
| 2009/0038701 A1 | 2/2009 | Delmotte |
| 2010/0016651 A1 | 1/2010 | Sivo |
| 2010/0113959 A1 | 5/2010 | Pascual-Leone |
| 2011/0054237 A1 | 3/2011 | Shapiro |
| 2012/0053555 A1 | 3/2012 | Ariagno et al. |
| 2013/0274707 A1 | 10/2013 | Wilmot et al. |
| 2016/0120528 A1 | 5/2016 | Abtin |
| 2018/0147355 A1 | 5/2018 | Larsen et al. |
| 2018/0207439 A1 | 7/2018 | Cook |
| 2019/0167910 A1 | 6/2019 | Buchine et al. |
| 2020/0009017 A1 | 1/2020 | Sharma |
| 2020/0016424 A1* | 1/2020 | Fan, I ............... A61N 2/004 |
| 2020/0222634 A1 | 7/2020 | Berry et al. |

FOREIGN PATENT DOCUMENTS

| | | |
|---|---|---|
| CN | 107427412 B | 7/2020 |
| CN | 112638446 A1 | 4/2021 |
| CN | 113692302 A | 11/2021 |
| DE | 1815118 A1 | 6/1970 |
| DE | 102005038495 A1 | 2/2007 |
| EP | 1093826 B1 | 12/2004 |
| EP | 2665502 B1 | 3/2020 |
| EP | 3820548 | 5/2021 |
| EP | 3921024 | 12/2021 |
| IL | 285455 | 9/2021 |
| IN | 502021 | 12/2021 |
| KR | 101899449 B1 | 9/2018 |
| WO | 2008087489 A2 | 7/2008 |
| WO | 2011011748 A1 | 1/2011 |
| WO | 2014145284 A2 | 9/2014 |
| WO | 2015142922 A1 | 9/2015 |
| WO | 2020014157 A1 | 1/2020 |
| WO | 2020163824 A1 | 8/2020 |

OTHER PUBLICATIONS

International Preliminary Report on Patentablility dated Jan. 12, 2021, International Application No. PCT/US2019/040882 filed Jul. 9, 2018.

Office Action dated Jul. 19, 2021, U.S. Appl. No. 16/504,325, filed Jul. 7, 2019.

Barbault et al., "Amplitude-modulated electromagnetic fields for the treatment of cancer: Discovery of tumor-specific frequencies and assessment of a novel therapeutic approach". Journal of Experimental & Clinical Cancer Research 2009, 28:51.

Binnewies et al., "Understanding the Tumor Immune Microenvironment (TIME) for Effective Therapy." Nature Medicine 24, 5 (Apr. 2018): 541-550.

Bohnert, Julia "Effects of Time-Varying Magnetic Fields in the Frequency Range 1 kHz to 100 kHz upon the Human Body. Numerical Studies and Stimulation Experiment", Karlsruhe Transactions on Biomedical Engineering, vol. 15.

Brahm et al., "The Current Status of Immune Checkpoint Inhibitors in Neuro-Oncology: A Systematic Review". Dancers 2020, 12, 586.

Buckner et al., "Inhibition of Cancer Cell Growth by Exposure to a Specific Time-Varying Electromagnetic Field Involves T-Type Calcium Channels", Plos One, DOI:10.1371.

Crocetti et al., "Low Intensity and Frequency Pulsed Electromagnetic Fields Selectively Impair Breast Cancer Cell Viability" PLoS ONE 8(9): e72944.

Delgado et al., "Embryological changes induced by weak, extremely low frequency electromagnetic fields". J. Anat. (1982), 134, 3, pp. 533-551.

(56) References Cited

OTHER PUBLICATIONS

Duan et al., "Turning Cold into Hot: Firing up the Tumor Microenvironment", Trends in Cancer, Jul. 2020, vol. 6, No. 7.
Filipovic et al., "Electromagnetic field investigation on different cancer cell lines". Cancer Cell International 2014, 14:84.
Gera et al., "Tumor Treating Fields Perturb the Localization of Septins and Cause Aberrant Mitotic Exit". PLoS ONE 10(5): e0125269.
Giladi et al., "Mitotic Spindle Disruption by Alternating Electric Fields Leads to Improper Chromosome Segregation and Mitotic Catastrophe in Cancer Cells" Scientific Reports, 5:18046.
Grasselly et al., "The Antitumor Activity of Combinations of Cytotoxic Chemotherapy and Immune Checkpoint nhibitors Is Model-Dependent". Front. Immunol. 9:2100.doi: 10.3389/fimmu.2018.02100.
Kim et al., "Tumor treating fields inhibit glioblastoma cell migration, invasion and angiogenesis". Oncotarget, vol. 7, No. 40.
Kirson et al., "Disruption of Cancer Cell Replication by Alternating Electric Fields," Cancer Research, vol. 64, 3288-3295, May 1, 2004, American Assoc, for Cancer Research, US.
Kong et al., "A Review of Anti-Angiogenic Targets for Monoclonal Antibody Cancer Therapy", Int. J. Mol. Sci. 2017, 18, 1786.
Kozisnnik et al., "Magnetic fluid hyperthermia: Advances, challenges, and opportunity". Int J Hyperthermia, 2013; 29 (8): 706-714.
Mafheo et al., "Lack of effect of weak low frequency electromagnetic fields on chick embryogenesis ", J Anat. Dec. 1984; 139(Pt4): 613-618.
Monache et al., "Inhibition of Angiogenesis Mediated By Extremely Low Frequency Magnetic Fields (ELF-MFs)," PLOS One, vol. 8, Issue 11, 1-11, Nov. 2013, PLOS, San Francisco, CA, US.
Newton et al., "Non-Invasive Radiofrequency Field Treatment of 4T1 Breast Tumors Induces T-cell Dependent nflammatory Response". Scientific Reports, 2018, 8:3474.
Nishimura et al., "Absence of reproductive and developmental toxicity in rats following exposure to a 20-kHz or 60-kHz magnetic field", Regulatory Toxicology and Pharmacology, vol. 64, Issue 3, Dec. 2012, pp. 394-401.
Nishimura et al., "Lack of Teratological Effects in Rats Exposed to 20 or 60 kHz Magnetic Fields", Birth Defects Research (Part B) 92:469-477 (2011).
Novocure, Inc., "Optunetm (NovoTTF-100A System) Patient Information and Operation Manual," 1-45, Portsmouth, NH, US.
Novocure, Inc.,"Instructions for Use, OPTUNETM (NovoTTF-100A System)," 1-27, Portsmouth, NH, US.
Ozen et al., "Low-frequency transient electric and magnetic fields coupling to child body". Radiation Protection Dosimetry (2008), vol. 128, No. 1, pp. 62-67.
Porat et al., "Determining the Optimal Inhibitory Frequency for Cancerous Cells Using Tumor Treating Fields KTTFields)", doi: 10.3791/55820.
Salari et al., "Towards non-invasive cancer diagnostics and treatment based on electromagnetic felds, optomechanics and microtubules". arXiv:1708.08339 [physics.med-ph].
Samoshree et al., "A Review on the Use of Magnetic Fields and Ultrasound for Non-invasive Cancer Treatment," Journal of Advanced Research, 14, 97-111, Jun. 2018, Elsevier, B.V.
Tatarov et al., "Effect of Magnetic Fields on Tumor Growth and Viability". Comparative Medicine, Aug. 2011, vol. 31, No. 4.
Vadala et al., "Mechanisms and therapeutic effectiveness of pulsed electromagnetic field therapy in oncology". Dancer Medicine 2016; 5(11):3128-3139.
Voloshin et al., Tumor-treating fields (TTFields) induce immunogenic cell death resulting in enhanced antitumor afficacy when combined with anti-PD-1 therapy.
Wenger et al., "A Review on Tumor-Treating Fields (TTFields): Clinical Implications Inferred from Computational Modeling". IEEE Reviews in Biomedical Engineering, 11, 195-207.
Zimmerman et al., "Targeted treatment of cancer with radiofrequency electromagnetic fields amplitude-modulated at tumor-specific frequencies". Chin J Cancer Nov. 2013;32(11):573-81.
Office Action dated Oct. 20, 2020, U.S. Appl. No. 16/784,239, filed Feb. 26, 2020.
Notice of Allowance dated Jan. 26, 2021, U.S. Appl. No. 16/784,239, filed Feb. 26, 2020.
Notice of Allowance dated Feb. 10, 2021, U.S. Appl. No. 16/784,239, filed Feb. 26, 2020.
International Search Report and Written Opinion dated May 8, 2020, International Application No. PCT/US2020/017365 filed Feb. 7, 2020.
International Search Report and Written Opinion dated May 8, 2020, International Application No. PCT/US2021/045132 filed Aug. 7, 2021.

* cited by examiner

Control @10x magnification

Cells exposed to 24 hour magnetic fields @10x magnification showing cell death

Average of 2 experiments (36 wells on a 96 well plate were exposed in each experiment)

SYSTEM AND METHODS FOR TREATING CANCER CELLS WITH ALTERNATING POLARITY MAGNETIC FIELDS

CROSS-REFERENCE TO RELATED APPLICATIONS

This application is a continuation application of U.S. application Ser. No. 16/784,239, filed Feb. 6, 2020, now U.S. Pat. No. 11,027,143, which claims the priority benefit of U.S. Provisional Application Ser. No. 62/802,685, filed Feb. 7, 2019. This application claims the priority benefit of both of the foregoing applications, which are each hereby incorporated by reference in their entirety.

TECHNICAL FIELD

The present invention involves treating rapidly proliferating or dividing cells, such as cancer cells, and more specifically to systems and methods for selectively inhibiting or destroying rapidly dividing cells by applying an alternating magnetic field having defined characteristics to a target area of a patient's body. Some embodiments of the invention provide a wearable system capable of providing an ambulatory therapy to a non-stationary patient by applying a magnetic field to inhibit or destroy rapidly dividing cells to the target body area.

BACKGROUND OF THE INVENTION

Cell division is a reproductive process in all living systems, including without limitation simple one-celled organisms such as bacteria and protozoa, as well as more complex organisms such as algae, plants, and animals, including humans. The cell division cycle involves a series of events within the cell that leads to a duplication of the DNA of the cell, with one of the duplicate DNA sequences going to each of two daughter cells. Prokaryotic cells are one-celled organisms that lack an enclosed nucleus and reproduce by a cell division process known as fission. More complex organisms with enclosed nuclei are called eukaryotes, whose cells asexually reproduce by a three-part cell division process involving periods known as interphase, mitosis, and cytokinesis. In the reproduction of sexual cells (i.e., egg and sperm) of more complex organisms, mitosis is replaced by meiosis.

During interphase, the parent cell produces nutrients and other components necessary for mitosis, and the DNA is duplicated as loosely packed chromatin. Mitosis involves separation of the duplicated DNA in the nucleus of the eukaryotic cell into two nuclei, each having a complete copy of the duplicated DNA. In cytokinesis, the cytoplasm, organelles & cell membrane are divided, forming two daughter cells of roughly equal size.

The process of mitosis is further divided into the stages of prophase, prometaphase, metaphase, anaphase, and telophase. In prophase, the DNA duplicated during interphase condenses into discrete long, thin chromosomes having two chromatids joined by a centromere. Each cell has two centrioles, which move to opposite poles of the cell during prophase. Microtubules radiate from near the two centrioles toward the center of the cell, including some which extend to the chromatids and help to separate the two chromatids into separate daughter chromatids. In metaphase, the chromosomes move toward the cell equator and align in the metaphase plane (or equatorial plane). The daughter chromatids separate from each other at the equator during early anaphase by moving along the microtubule spindle fibers toward the centromeres at opposite poles of the cell, a process which elongates the cell. In late anaphase the daughter chromosomes each reach their opposite poles of the cell, and the cell membrane begins to pinch to form the two daughter cells, which is part of cytokinesis, or the process by which the daughter cells are separated. During telophase, the microtubules continue to lengthen and a new nuclear envelope forms around each of the separated daughter chromosomes, each of which has an identical set of chromosomes, and cytokinesis proceeds with further pinching of the two daughter cells toward becoming separate entities. By the end of telophase, the microtubule spindles disappear. Finally, the daughter cells fully separate, completing cytokinesis.

Cancer cells and some non-cancerous cells (e.g., non-malignant tumors) proliferate or grow in an uncontrolled manner in contrast to normal cells. In addition to the extra space such tumors or cells occupy, they may also damage nearby normal cells. Cancer cells may also metastasize, traveling to other locations in the body, where they continue to hyperproliferate and may form new tumors. The rapid growth of tumors and cancer cells results from their rapid rate of cell division compared to normal cells.

Many effective anti-cancer and anti-tumor therapies are based on the fact that cells in the process of dividing are more sensitive to radiation and many drugs than non-dividing cells. Because tumor cells divide much more frequently than normal cells, it is possible, by using therapies that act on tumor cells while they are dividing, to selectively damage or destroy them while leaving normal cells—which divide less frequently—less affected. However, because many types of cancer cells are only slightly more susceptible to radiation and/or chemotherapy agents than normal cells, it is not always possible to selectively affect tumor cells while leaving normal cells unaffected. Consequently, many radiation and chemotherapy agents significantly damage normal cells as well as tumor cells, leading to a significant patient burden (e.g., pain, scarring, organ damage, blood damage, impaired immune system function, etc.) for even "successful" treatments.

In addition to radiation and chemotherapeutic agents, other therapies involving different modes of action have been used to treat tumor cells, including without limitation ultrasonic and electrical therapies. Electrical currents and electrical fields have been used for decades for medical purposes.

One type of electrical therapy involves applying an electrical current through body tissue separated by two or more conductive electrodes. This type of therapy may be used, for example to stimulate or excite muscle or nerve tissue (e.g., pacemakers, defibrillators, neurostimulators) or to generate heat within a desired body tissue (e.g., thermal therapies to remodel collagen or to ablate tissue). Electrical therapies involving conductive electrodes may involve direct current or alternating current at a wide range of frequencies (e.g., less than 1 Hz to above 1 MHz). The energy from electrical currents is delivered to tissue based on the electrical conductive characteristics (e.g., resistance, capacitance) of the tissue. Since these properties are similar for both tumor and normal cells, such therapies affect both tumor and normal cells (e.g., destroying both by heat if they are within the current path) in the same manner. At lower frequencies (typically below 20 kHz), the use of conductive electrodes may be used to stimulate muscle or nerve tissue to activate muscle or nerve fibers. At frequencies used in many electrical therapies (e.g., tens of kHz to MHz), stimulation with conductive electrodes is too rapid for stimulation signals to propagate through such tissue and the signals are "shorted."

Another medical use of electrical energy involves the use of insulated electrodes to deliver high frequency electrical energy radiatively or inductively to target tissue. For example, radio frequency (RF) or microwave energy may be applied radiatively to tissue through the air or another electrically insulating material separating the electrodes from the tissue being treated. The effect of this type of electrical energy on living tissue is based on the dielectric properties of the tissue rather than their conductive characteristics.

More recently, insulated electrodes have been used to treat cancer cells and other rapidly proliferating cells by applying AC electric fields at frequencies of 50-500 kHz and electric field strengths of about 10-1000 V/m to a target body area that includes such cells. Such therapy is often referred to as TC ("tumor curing") field or TTF ("tumor treatment field") therapy. In U.S. Pat. No. 6,868,289, which is hereby incorporated by reference in its entirety, a method and apparatus are disclosed for destroying rapidly proliferating cells using insulated electrodes to generate an electric field. At electric field frequencies of 50-500 kHz, the cell membranes of the dividing cells act to concentrate the electric field lines at the cleavage furrow separating the two daughter cells of the dividing cell. The high-density field at the cleavage furrow causes polarized or charged intracellular components within the cell to move toward the high-density field lines at the cleavage furrow, eventually disrupting the cell membrane at the cleavage furrow, and destroying the dividing daughter cells.

In U.S. Pat. No. 8,019,414, which is hereby incorporated by reference in its entirety, a method of killing or destroying cancer cells is disclosed that involves applying an electric field together with another cancer therapy such as radiation or chemotherapy drugs. The electrical field may be a field such as that disclosed in the '289 patent.

The use of electric fields to destroy cancer cells, while effective at certain frequencies and electrical field strengths, is limited in many practical respects. To provide a safe and consistent electrical field strength, the electrodes of systems such as those disclosed in the '298 and '414 patents must be in intimate contact with the tissue (e.g., skin) of the patient at all times during the treatment. To ensure good contact with the patient's skin, it may be necessary to shave all hair from the skin to which the electrodes are coupled. Because the therapy may be delivered for an extended period of time, the electrodes frequently cause skin irritation at the electrode contact site. For example, in one recent study of TTF therapy, forty-three percent (43%) of patients experienced some skin irritation, with 1% reporting severe skin irritation. The relatively high incidence of skin irritation or pain may prohibit the therapy in sensitive body areas (e.g., breast tissue, etc.). TTF therapy also involves the use of relatively high voltages. For this reason, patients must be careful in performing everyday activities having a risk of water exposure (e.g., showering, exercise (sweating), or even exposure to rain).

The use of electrodes in direct contact with the patient's skin presents a risk of burning or heating of tissue adjacent to the electrodes. Because of this risk (and buildup of dirt, oils, etc.), the electrodes in TTF therapy systems typically require frequent replacement (e.g., twice each week). Patients wearing TTF electrodes on the scalp reported headaches related to wearing the electrodes 24 hours a day.

TTF electrodes must also be placed by trained users (e.g., technicians or physicians). Because the treatment is highly localized (i.e., between the electrodes), precise location of the cancer/tumor must first be performed, and the electrodes must be placed with a high degree of accuracy to create an electric field that passes through it. If the electrodes are slightly off of optimal placement, the treatment may result in suboptimal results.

In addition, although the '289 patent discloses ambulatory embodiments (i.e., embodiments in which the patent can wear and use the system in performing at least some ordinary non-stationary life activities such as walking, driving, shopping, etc.), in practice the power requirements (e.g., high voltages) for generating appropriate electric fields (e.g., at least 10 V/m) result in bulky and/or heavy electronics boxes that must be coupled to the electrodes and thus carried by the patient. One clinical study showed a relatively high rate of falls in patients carrying these cumbersome TTF electronics boxes.

In view of these limitations to TTF systems, there is a need for safer therapies that may be applied for longer durations to destroy cancer or other rapidly-dividing cells. The many problems associated with electrodes also raise a need for new therapies that avoid a risk of skin pain or the need for continuous contact with skin or other tissue. Because the efficacy of the system depends upon how long the electric fields can be applied to the rapidly-dividing cancer cells, less bulky, heavy, and cumbersome systems are needed to permit truly ambulatory, long duration treatments. Finally, there is a need for therapy systems that do not require trained patients or clinicians for setup.

SUMMARY

In one aspect, the present invention provides a method of treating cancer cells in a target body area of a patient's body comprising: coupling a magnetic field generator to the target body area of the patient's body; and applying an alternating polarity (AP) magnetic field to the target body area using the magnetic field generator, the AP magnetic field having a frequency of 0.5-500 kHz and a magnetic field strength of 0.05-5 milliTesla (mT), wherein the AP magnetic field selectively affects the cancer cells to achieve at least one of damaging the cancer cells, inhibiting the growth of the cancer cells, reducing tumor size, inhibiting angiogenesis, or preventing metastasis of the cancer cells, while leaving non-cancer cells substantially unharmed.

In another aspect, the present invention provides a system for treating cancer cells in a target body area of a patient's body comprising: at least one alternating polarity (AP) electromagnetic coil coupled to a target body area of the patient's body; a power supply for supplying power to said at least one AP electromagnetic coil; and a controller for controlling the at least one AP electromagnetic coil and power supply to generate and apply to the target body area an AP magnetic field having a frequency of 0.5-500 kHz and a field strength of 0.05-5 mT, wherein the AP magnetic field selectively affects the cancer cells to achieve at least one of damaging the cancer cells, inhibiting the growth of the cancer cells, reducing tumor size, inhibiting angiogenesis, or preventing metastasis of the cancer cells, while leaving non-cancer cells substantially unharmed.

In another aspect, the present invention provides a system for treating cancer cells in a target body area of a patient's body comprising: at least one alternating polarity (AP) electromagnetic coil coupled to a target body area of the patient's body; a retaining element to which the at least one AP electromagnetic coil is coupled, wherein the retaining element is adapted to maintain the at least one AP electromagnetic coil in a desired position relative to the target body area; a power supply for supplying power to said at least one AP electromagnetic coil; and a controller for controlling the at least one AP electromagnetic coil and power supply to generate and apply to the target body area an AP magnetic field having a frequency of 0.5-500 kHz and a field strength of 0.05-5 mT, wherein the AP magnetic field selectively affects the cancer cells to achieve at least one of damaging the cancer cells, inhibiting the growth of the cancer cells, reducing tumor size, inhibiting angiogenesis, or preventing metastasis of the cancer cells, while leaving non-cancer cells substantially unharmed.

DESCRIPTION

Figure 1:
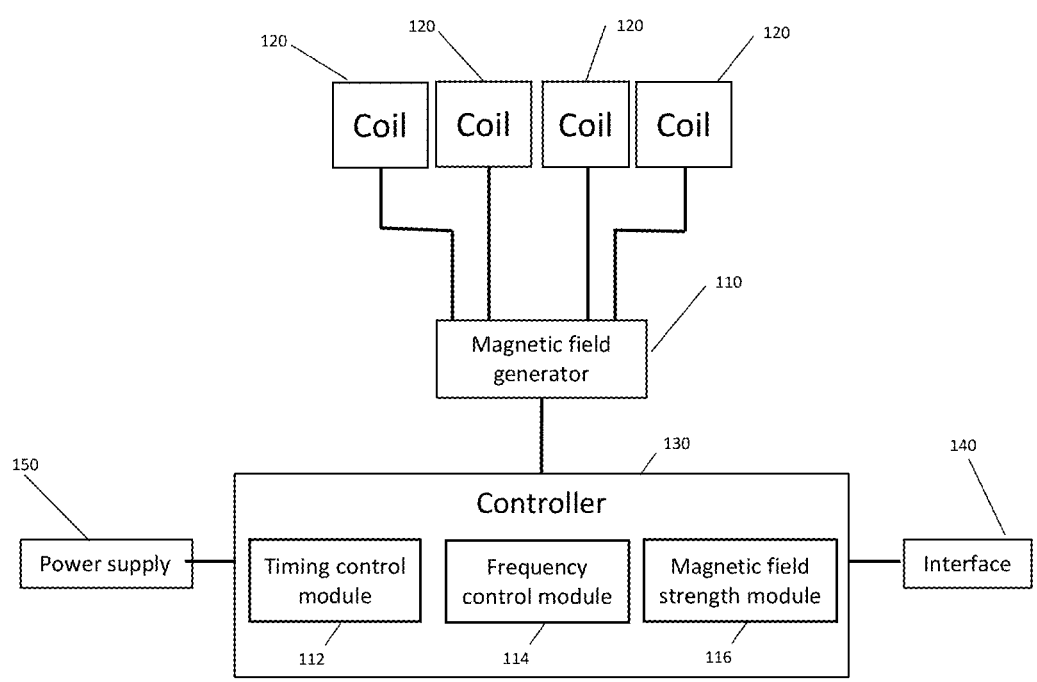
FIG. 1 is a schematic block diagram of a system for providing an alternating polarity (AP) magnetic field to a target body area of a patient's body, according to one embodiment for selectively destroying cells.

Exemplary embodiments of the present disclosure are illustrated in the drawings, which are illustrative rather than restrictive. No limitation on the scope of the technology or on the claims that follow is to be implied or inferred from the examples shown in the drawings and discussed here.

In some embodiments, the invention provides apparatus and methods for treating a patient having cancer or other rapidly dividing cells (e.g., bacterial infection) in a target body area using alternating polarity (AP) magnetic fields at specified frequencies to destroy or inhibit the proliferation of the rapidly dividing cells. The use of electric fields, including without limitation TTF systems, to treat patients having cancer or other diseases characterized by rapidly-dividing cells has a number of limitations that make treatment for some patients difficult, ineffective, painful, or unsafe. Embodiments of the present invention overcome one or more of these limitations by using AP magnetic fields to treat rapidly-dividing or hyperproliferating cells.

As used herein, the terms "magnetic field tumor (MFT) therapy" and "MFTT" refer to systems and methods for treating cancer or other rapidly-dividing cells with AP magnetic fields at specified frequencies and magnetic field strengths to destroy or inhibit the proliferation of such cells. In various embodiments, the present invention may be used to treat one or more cancers such as throat cancer, thyroid cancer, mouth cancer, nose cancer, salivary gland cancer, lung cancer, lung carcinoid tumors, thymic malignancies, tracheal tumors, pancreatic cancer, liver cancer, stomach cancer, kidney cancer, ovarian cancer, prostate cancer, colon cancer and rectal cancer.

FIG. 1 is a simplified schematic block diagram illustrating certain components of an MFT therapy system 100 according to an embodiment of the invention. The MFT therapy system 100 includes an alternating polarity magnetic field generator (APMFG) 110 to generate an electrical signal to energize one or more alternating polarity (AP) electromagnetic coils 120 to produce an AP magnetic field having specified frequency and field strength characteristics. In one embodiment, the AP electromagnetic coils 120 may have sizes and shapes adapted to engage one or more target body areas of a patient (e.g., torso, breast, head, neck, throat) for treatment of cancer or hyperproliferating cells in the target body area. The electrical signals generated by APMFG 110 and applied to AP electromagnetic coils 120 is controlled by a controller 130, which specifies the parameters of the magnetic fields to be generated by APMFG 110 and AP electromagnetic coils 120, and controls the function and operation of the system 100. An interface 140 is provided to allow a user to specify treatment parameters to be programmed or communicated to the controller 130, and to receive information from the controller relating to the operation and status of the MFT therapy system 100. A power supply 150 provides power to MFT therapy system 100. Power supply 150 may be selected from a variety of known power supplies, and may comprise, in various embodiments, a battery such as a disposable or rechargeable battery, or a power source such as a standard 120V, 60 Hz electrical power outlet in the US, together with circuitry for regulating the power at appropriate currents and voltages for each of the APMFG 110, AP electromagnetic coils 120, controller 130, and interface 140.

Controller 130 may include circuitry and other components (e.g., microcontrollers, resistors, registers, memory, firmware, software, etc.) to direct and control the operations of the APMFG 110, AP electromagnetic coils 120, and interface 140. FIG. 1 illustrates an embodiment in which the AP electromagnetic coils 120 are energized directly from the magnetic field generator. In an alternative embodiment (not shown), controller 130 may communicate directly with each of the one or more AP electromagnetic coils 120 to control their operation in whole or in part (e.g., by switches that enable or disable each AP electromagnetic coil 120).

Controller 130 includes a timing control module 112 for controlling the timing of the MFT therapy delivered by AP electromagnetic coil(s) 120 to one or more target body areas or tissues. In various embodiments, timing control module 112 may cause the AP magnetic field generator 110 and AP electromagnetic coils 120 to provide MFT therapy for a programmed duration such as 1-100 hours or other treatment period, or the timing of and between a plurality of therapy treatment periods. For example, the timing control module 112 may implement a first therapy for a first time period (e.g., during waking hours of the patient) at a first frequency and field strength, followed by a second time period in which no therapy is applied, followed by a third time period in which a second therapy is implemented at a second frequency and second field strength. Timing control module 112 may also control the timing of changes in other treatment parameters, such as changes in the frequency or field strength of the MFT therapy applied to the patient.

A frequency control module 114 controls the frequency of the AP magnetic fields delivered by AP electromagnetic coil(s) 120 to the one or more target body areas or tissues. Frequency control module 114 may control the frequency of the AP magnetic field at a programmed frequency of 0.5-500 kHz. In some embodiments, the frequency control module 114 may control frequency changes to the AP magnetic fields generated by the APMFG 110 and the AP electromagnetic coils 120 at a programmed rate of change or according to specific frequency step changes.

A magnetic field strength control module 116 controls the field strength of the AP magnetic fields applied to the one or more target body areas. Magnetic field strength control module 116 may control the field strength at a programmed magnetic field strength of 0.05-5 mT, and may control changes in the field strength according to a programmed rate of change or programmed step changes in field strength.

Controller 130 may include programming logic, timers, and other circuitry to accomplish the functions of the timing control module 112, frequency control module 114, and magnetic field strength control module 116. It will be appreciated in alternative embodiments, the functions of all or portions of timing control module 112, frequency control module 114, and magnetic field strength control module 116 may be combined into one or more submodules, or implemented by controller 130 as a whole.

In one embodiment, interface 140 may include a user input, such as a keyboard or buttons, to allow a user to input or receive data from controller 130. In a further embodiment (not shown,) interface 140 may be located within controller 130 and may comprise a transceiver to communicate with a separate user device (not shown) such as a cell phone, tablet, or other computing device to program the MFT therapy system 100 and receive data therefrom (e.g., operating and alarm status flags, programmed parameters, treatment time, etc.). In other alternative embodiments (not shown), interface 140 may be omitted, or may be incorporated as part of a single unit having some or all of the functions of AP magnetic field generator 110, controller 130, and interface 140.

Referring again to FIG. 1, in various embodiments the APMFG 110 may provide an electrical signal to cause each of the one or more AP electromagnetic coils 120 to generate magnetic fields having one or more fixed or variable AP frequencies. Although shown in the simplified schematic diagram of FIG. 1 as coupled to APMFG 110 by a single wire, it will be understood that each of AP electromagnetic coils 120 will generally be coupled to APMFG 110 by a pair of wires (not shown) to provide a complete circuit. In fixed-frequency embodiments, APMFG 110 may cause each of the one or more AP electromagnetic coils 120 to generate a magnetic field having a single frequency or a plurality of frequencies either continuously or intermittently according to a defined duty cycle (e.g., having a programmable on-time during which the magnetic field is emitted from AP electromagnetic coils 120, followed by an off-time during which no field is emitted). The APMFG 110 may also cause the one or more AP electromagnetic coils 120 to generate AP magnetic fields having a variety of waveforms, e.g., sinusoidal, triangular, trapezoidal etc. In some embodiments the APMFG 110 may cause the one or more AP electromagnetic coils 120 to generate AP magnetic fields having a predefined number of waveforms of a specified first frequency, and repeat this pattern at a second specified frequency (burst mode). In other embodiments, the APMFG 100 may cause the one or more AP electromagnetic coils 120 to generate a magnetic field having a waveform which uses a fixed frequency or a combination of frequencies coupled with amplitude modulation.

Whether fixed or variable, the frequency (or frequencies) of the AP magnetic fields generated by each AP electromagnetic coil 120 are preferably frequencies below about 1 MHz, and more preferably are frequencies within the range of 0.5-500 kHz, more preferably within the range of 25-400 kHz, and still more preferably within the range of 100-300 kHz. In one embodiment, the MFT therapy system 100 may comprise at least two AP electromagnetic coils 120, each having a fixed or variable frequency within a different frequency range to provide magnetic fields at multiple frequencies to a target body area or tissue. For example, APMFT 110 may generate a first electrical signal to cause a first AP electromagnetic coil 120 to generate an AP magnetic field with a first fixed frequency or a variable first frequency within a first frequency range, and a second electrical signal to cause a second AP electromagnetic coil 120 to generate an AP magnetic field with a second fixed frequency or a variable second frequency within a second frequency range, where both the first frequency range and the second frequency range are ranges within the range of 0.5-500 kHz. As a nonlimiting example, the first range may be a low-frequency range (e.g., 1-5 kHz) and the second frequency range may be a higher-frequency range (e.g., 50 kHz-300 kHz).

Without being bound by theory, it is believed that AP magnetic fields within a plurality of frequency sub-ranges within the range of 0.5-500 kHz may affect different aspects of the reproduction cycle of rapidly-dividing cells, and that each such aspect may be more strongly affected by AP magnetic fields within a particular frequency sub-range within the broader range of 0.5-500 kHz. For example, the interruption of angiogenesis by extremely low frequency AP magnetic fields has been reported for AP magnetic fields having a frequency of 50 Hz (Monache et al., "Inhibition of Angiogenesis Mediate by Extremely Low-Frequency Magnetic Fields (ELF-MFs)," PLOS One, 8:11 (November 2013). Different types of cells, including without limitation different types of cancer cells, may require different frequencies for interruption of angiogenesis.

Accordingly, in one embodiment an MFT therapy having a bimodal magnetic field frequency distribution may be applied to the target body area. In one exemplary embodiment, the APMFT 110 may generate a first electrical signal to cause a first AP electromagnetic coil 120 to generate a first variable AP magnetic field distribution that varies the magnetic field frequency over a first time period (e.g., 1 second, 1 minute, 10 minutes, 1 hr) between a first lower limit (e.g., 0.5 kHz) and a first upper limit (e.g., 5 kHz) to broadly interrupt a first metabolic process (e.g., angiogenesis) in a target cell population, as defined by frequency control module 114. The APMFT 110 may also generate a second electrical signal to cause the same or a second AP electromagnetic coil 120 to generate a second variable AP magnetic field distribution that varies the magnetic field frequency over a second time period (e.g., 1 second, 1 minute, 10 minutes, 1 hr) between a second lower limit (e.g., 50 kHz) and a second upper limit (e.g., 400 kHz) to broadly interrupt a second metabolic process (e.g., the mitosis cycle) of rapidly-dividing cells. Additional coils may produce different fixed or variable-frequency AP magnetic fields having different frequencies or frequency ranges to interrupt still other aspects of the reproduction cycle of rapidly-dividing cells. In an alternative example, a single AP electromagnetic coil 120 may be used to sequentially deliver AP magnetic fields within two different AP frequency ranges (e.g., 1-5 kHz for a first treatment period, followed by 50-400 kHz for a second treatment period).

In variable-frequency embodiments, many different ways of implementing a changing frequency are possible, and enumeration herein of specific embodiments of varying frequencies is illustrative and is not intended to be limiting. It will be appreciated that additional variable-frequency embodiments may be implemented in view of the present disclosure. In one embodiment, a magnetic field may be generated having a single frequency that varies from a lower frequency (e.g., 50 kHz) to an upper frequency (e.g., 250 kHz) in a uniform manner (i.e., non-varying rate of frequency change) within a defined frequency range time period or at a desired (e.g., programmed) frequency change rate. In another embodiment, the frequency may vary in a non-uniform manner such as stepwise changes in frequency or different rates of change (e.g., rates of change of frequency are highest near the mid-point between the upper and lower frequency limits). In a still further embodiment, the frequency may vary continuously or intermittently, with variable-frequency periods alternating with non-variable frequency periods. In additional embodiments, a field having two different frequencies may simultaneously be applied to the target body area (emitted, e.g., by a single coil or by two different coils). By providing multiple (e.g., 2 or more) coils, MFT therapies having a desired frequency distribution (e.g., random, Gaussian, or non-Gaussian) either sequentially or simultaneously may be applied to one or more target areas.

The electrical signal from APMFG 110 to AP electromagnetic coils 120 also defines the field strength of the AP magnetic fields produced by the coils, as defined by magnetic field strength control module 116. MFT therapy systems 100 of the present invention may use relatively low magnetic field strengths to destroy or impair rapidly-proliferating cells. Preferably, MFT therapy fields in systems 100 of the present invention have field strengths of less than 5 milliTesla (i.e., 5,000 μT), such as field strengths within the range of 0.05-5 mT. In a preferred embodiment, the field strengths are within the range of 0.2-2 mT, and more preferably within the range of 0.5-1.2 mT.

In one embodiment, the magnetic field may have a single, non-varying field strength. Without being bound by theory, it is believed that different cell sizes (e.g., different types of cancers) may require different field strengths for maximum efficacy in destroying or inhibiting cell division. Within such embodiments, however, the AP magnetic fields may have a single, non-varying field strength either continuously or intermittently according to a defined duty cycle as defined by, e.g., timing control module 112 and magnetic field strength control module 116.

In variable-field-strength embodiments, many different ways of varying the field strength can be envisioned, similar to the variations described above respecting frequency changes. As with frequency, enumeration herein of specific embodiments of varying field strength is illustrative, not limiting. Additional variable-field-strength embodiments may be implemented (e.g., by magnetic field strength control module 116) in view of this disclosure. In one embodiment, a magnetic field may have a field strength that varies from a lower limit (e.g., 0.05 mT) to an upper limit (e.g., 1 mT) in a uniform manner (i.e., with a non-varying rate of change) within a defined field strength range time period. In another embodiment, the field strength may vary in a non-uniform manner such as stepwise changes in field strength or with a swept field strength variation with accelerating or decelerating field strength variation (e.g., rates of change of field strength are highest near the upper and lower limits of the field strength range). In a still further embodiment, magnetic field strength may vary continuously or intermittently, with variable-field-strength periods alternating with non-variable-field-strength periods. In some embodiments, AP magnetic fields at two different frequencies, each having a different field strength, may simultaneously be applied to the target body area (emitted, e.g., by two different AP electromagnetic coils 120). By providing multiple AP electromagnetic coils 120, MFT therapies having a desired frequency and magnetic field strength distribution (e.g., random, Gaussian, or non-Gaussian), either sequentially or simultaneously may be applied to the target body area.

Because MFT therapies act only on dividing cells, overall efficacy corresponds to lengthy treatment periods (e.g., many hours or days, and in some cases weeks). However, to minimize damage to normal (e.g., non-cancerous or non-tumor) cells, in some embodiments the therapy is suspended for certain periods. This may involve, for example, providing MFT therapy continuously with defined alternating on-time (e.g., a time period withing a range of 1 sec-24 hr) and off-time (e.g., 1 sec-24 hr) periods according to a defined treatment duty cycle as defined by timing control module 112. In one embodiment, the on-time and off-time periods may be a time period within a range of 1 second-1 week, 1 sec-24 hr, 1 minute-12 hr, etc.). In one such exemplary embodiment, the MFT therapy is provided continuously at a 10:1 duty cycle by generating and applying the MFT therapy fields for ten (10) minutes, followed by 1 minute in which no therapy is applied, with the process repeated until a predefined total treatment duration (e.g., 2 weeks) is complete. In another embodiment, the same 10:1 duty cycle may be administered by applying the MFT therapy fields for ten hours, followed by a one-hour suspension of therapy, and repeating the process until the total treatment period is complete.

In another embodiment, MFT therapy according to a defined treatment duty cycle comprising on-time and off-time periods may be administered for a defined treatment duration (e.g., 1 hr, 6 hr, 8 hr, 24 hr) after which no further treatment is applied. In a still further embodiment, the MFT therapy may be administered according to the patient's circadian rhythms (e.g., continuously at night or when the patient is sleeping, and according to a defined duty cycle for defined periods during the day such as morning hours, afternoon hours, or evening hours). It will be appreciated that other duty cycles and treatment durations may be used, and that the therapy may involve, as previously discussed, constant or variable magnetic field frequencies and field strengths.

In another embodiment, MFT therapy may be applied according to a defined treatment duty cycle of on-time and off-time periods, with the magnetic field strength varying according to a defined field strength duty cycle. This may involve, for example, a 10:1 treatment duty cycle combined with a 4:1 field strength duty cycle. As a specific example, the MFT therapy may be provided for a 24 hr treatment duration, at a 10:1 treatment duty cycle with AP magnetic fields applied to a target body area for 10 minutes, followed by 1 minute in which no AP magnetic fields are applied. Within the 10 minute treatment periods, 8 minutes may involve variable frequency treatment within a first field strength range of 3.0-4.0 mT, followed by 2 minutes of treatment within a second field strength range of 0.5-1.5 mT, providing a 4:1 field strength duty cycle.

In alternative embodiments, MFT therapy fields may be applied according to the patient's circadian rhythms, or according to specific times of day. For example, the MFT therapy fields may be applied to the target body area only during daytime hours; only during nighttime hours; during all daytime hours except during mealtime hours; during all daytime hours except when the patient is exercising (as detected by, e.g., an activity monitor); during specific hours of the day (e.g., 9:00 AM-noon and 6:00 PM-5:00 AM). These examples are intended to be exemplary only, and it will readily be appreciated that delivery of MFT therapy fields can be tailored to suspend therapy during certain hours that would be most convenient to the patient, while also minimizing damage to normal (i.e., non-rapidly-dividing) cells.

Most magnetic field-generating coils are constructed so as to generate a magnetic field having an axis along which the magnetic field lines are directed. In some embodiments, multiple AP magnetic coils 120 can be spatially aligned in such a manner that a desired magnetic field distribution is generated in area of interest, such as the entirety or a portion of the target body area.

In some embodiments, one or more parameters defining the MFT therapy (e.g., frequency, field strength, selection of specific coils among a plurality of available coils) may be determined based on the results of certain tests. For example, an imaging procedure may be performed to identify the type and location of the target rapidly-dividing cells (e.g., cancer or tumor cells). In various embodiments, the imaging procedure may be an imaging procedure using one or more of an MRI system, a CT scan system, a PET scan system, and an X-ray system.

Based on the results of the imaging (e.g., cell size(s), type of cells, location of cells, etc.) a healthcare provider such as a physician may select one or more parameters of the MFT therapy, including without limitation, the frequency/frequencies of the magnetic field(s), the field strength(s), the positioning of one or more coils, a coil size, a type of retaining element (e.g., a garment type) to maintain the coils in position relative to the target body area, a duty cycle or schedule for applying therapy, etc. It will be appreciated that the foregoing and other parameters may also be selected based on other tests, e.g., a pathological analysis of the cancer cells such as a microscopic analysis of a biopsy, a chemical test, a genetic test, etc.

In some instances, the results of an imaging procedure prior to the MFT therapy may identify a target body area to which MFTT is to be directed. Based on the location of the target body area, in some embodiments a retaining element may be necessary to retain the magnetic coils in a desired position relative to the target treatment area or tissue. Various retaining elements may be used to unobtrusively and securely maintain the magnetic coils in a desired position relative to a desired target area of the patient's body. For example, a bra may be used to house the magnetic coils for treatment of breast cancer cells. In another example, a hat may be used to retain magnetic coils in position to treat brain cancer. In still another example, a neck cuff, collar, or scarf may retain one or more magnetic coils for treatment of esophageal cancer, and a shirt may be used to retain one or more magnetic coils to treat lung cancer. In another embodiment, the retaining element may be a bandage such as an adhesive bandage capable of adhering to the target body area or to skin adjacent thereto. These examples are exemplary and not limiting, and it will be appreciated that a variety of other or additional retaining elements may be used depending upon the target tissue location. Because the magnetic coils do not need to be in direct contact with the skin of the patent, the retaining elements may include pouches or pockets for securely retaining the coils in position with a comfortable and biocompatible lining placed between the coil and the skin or target treatment area. In some embodiments, the AP electromagnetic coils 120 are completely integrated within the retaining element during manufacturing (e.g., the coils are completely integrated inside a garment such as a bra, hat, shirt, bandage, etc.) In various embodiments, the retaining element may include a lead wire for coupling each of the one or more coils 120 to the AP magnetic field generator 110 and/or controller 130. In alternative embodiments, a direct electrical coupling (e.g., a snap fit) may be used between an electronics package and the AP electromagnetic coil(s) 120. The electronics package may include one or more of the power supply 150, controller 130, APMFG 110, and interface 140.

Figure 2:
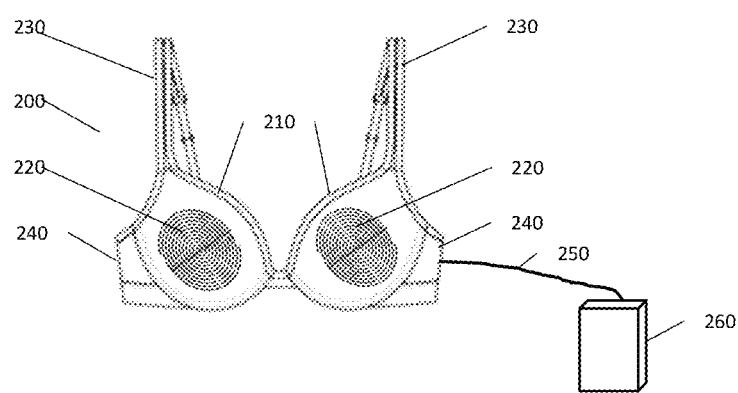
FIG. 2 is a front view of a retaining element comprising a bra having one or more AP electromagnetic coils for providing an AP magnetic field to breast tissue, according to one embodiment of the invention.

FIG. 2 illustrates a bra 200 that acts as a retaining element for one or more magnetic coils 220 for applying one or more magnetic fields to a target body area to treat cancer cells or other rapidly-dividing cells in breast tissue. Magnetic coils 220 may be the same as coils 120 described in FIG. 1, but may be adapted for placement in bra 200 (e.g., with a size, geometry, etc., for treatment of breast tissue). Bra 200 may in many aspects be constructed similarly to existing bras available at retail clothing outlets, and may include cups 210 for holding breast tissue and retaining coils 220 in position relative to a target body area comprising breast tissue. Straps 230 may be provided to secure the bra 200 to the shoulders of the patient, and side straps or bands 240 for securing the bra to the patient's torso. AP electromagnetic coils 220 may be integrated into bra 200, or may be removably coupled thereto.

One or more cables or wires 250 may be provided to couple each of the coils 220 to an electronics box 260, which may house the remaining components of the MFT therapy system 100 of FIG. 1 such as APMFG 110, controller 130, power supply 150, and in some embodiments interface 140. In alternative embodiments, one or more of the APMFG 110, controller 130, power supply 150, or interface 140 may be provided separately from the electronics box 260. For example, interface 140 may comprise a mobile phone app that communicates directly with one or more of APMFG 110, controller 130, power supply 150, etc., as well as receiving and displaying information from one or more of the foregoing system components. The mobile phone app interface may allow the patient or a healthcare provider to program one or more treatment parameters for the MFT therapy system 100, and may display information relating to the MFT therapy or system 100 status (e.g., displaying how long the MFT therapy has been applied, whether a magnetic field is currently being applied to the target tissue from each of the coils 220, the frequency and/or field strength of the currently-provided magnetic fields, remaining battery life, etc.).

Figure 3:
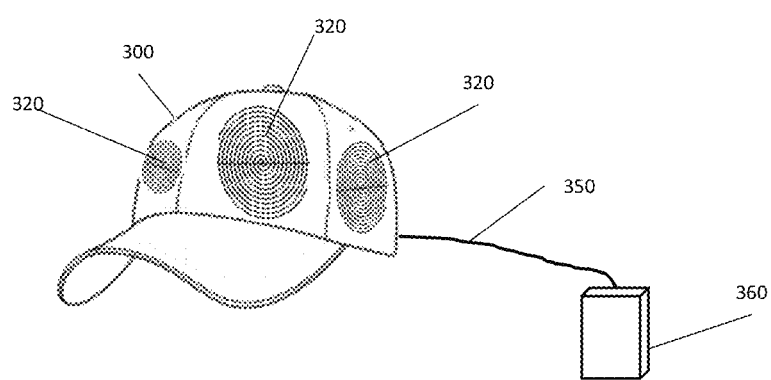
FIG. 3 is a front view of a retaining element comprising a hat including one or more AP electromagnetic coils for providing an AP magnetic field to brain tissue, according to one embodiment of the invention.

FIG. 3 illustrates a hat 300 that acts as a retaining element for one or more AP electromagnetic coils 320 for applying one or more magnetic fields to the treatment of cancer or other rapidly-dividing cells in a target body area comprising brain tissue. Magnetic coils 320 are, in one embodiment, similar to AP electromagnetic coils 120 described in FIG. 1, but may be adapted for placement in hat 300. This may include changes in the size, geometry, or other characteristics to enable effective placement in hat 300 for treatment of brain tissue. Although depicted as a baseball cap, it will be apparent that many other hat types and styles may be used for hat 300 (e.g., skullcap, beret, fedora, etc.). In one embodiment, hat 300 may be a skullcap of an appropriate size to fit closely on the head of the patient, and the magnetic coils 320 may have a concave shape adapted for location or placement in the cap, e.g., inside the hat or in a pocket between an inner and outer layer thereof. AP electromagnetic coils 320 may be integrated into hat 300, or may be removably coupled thereto.

One or more cables or wires 350 may be provided to couple each of the AP coils 320 to an electronics box 360, which may house the remaining components of the MFT therapy system 100 of FIG. 1 such as APMFG 110, controller 130, power supply 150, and in some embodiments interface 140. In alternative embodiments, one or more of the APMFG 110, controller 130, power supply 150, or interface 140 may be provided separately from the electronics box 360. For example, as described in connection with FIG. 2, a separate interface 140 may be provided as a mobile phone app that communicates directly with one or more of APMFG 110, controller 130, power supply 150, etc. Such an app-based interface may also provide information on the MFT therapy to the patient or a healthcare provider (e.g., displaying how long the MFT therapy has been applied, whether a magnetic field is currently being applied to the target tissue from each of the coils 320, the frequency and/or field strength of the currently-provided magnetic fields, remaining battery life, etc.).

Figure 4:
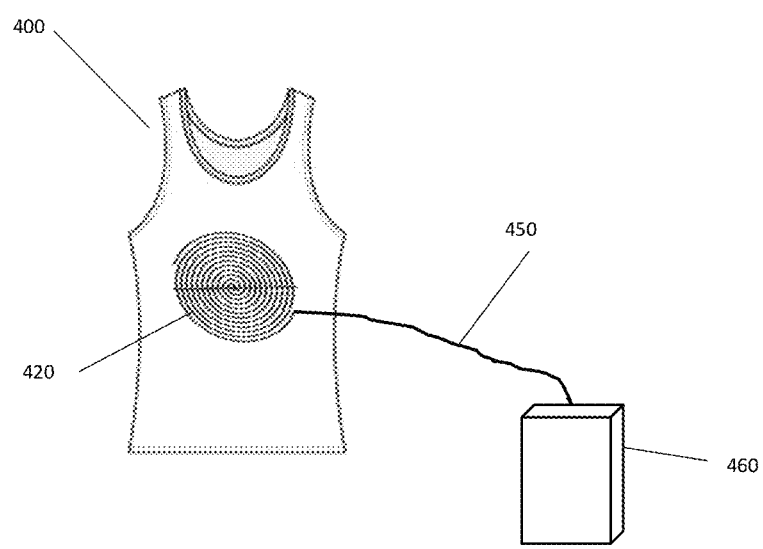
FIG. 4 is a front view of a retaining element comprising a shirt having one or more AP electromagnetic coils for providing an AP magnetic field to thoracic or abdominal tissue, according to one embodiment of the invention.

FIG. 4 illustrates a shirt 400 that acts as a retaining element for one or more AP electromagnetic coils 420 for applying one or more magnetic fields to the treatment of cancer or other rapidly-dividing cells in a target tissue in a patient's thoracic or abdominal region. This may include, without limitation and depending on the placement of the one or more AP electromagnetic coils 420, treatment of lung cancer, liver cancer, pancreatic cancer, or cancers or tumors in other thoracic or abdominal organs or structures. AP electromagnetic coils 420 are, in one embodiment, similar to coils 120 described in FIG. 1, but may be adapted for placement in shirt 400 based on the target tissue. This may include changes in the coil size, geometry, or other characteristics to enable effective placement in shirt 400 and for treatment of the particular target tissue. Although depicted as a T-shirt, that many other types and styles of shirt may be used as shirt 400, including long-sleeve or short sleeve shirts; button, zip, or pullover shirts. In addition, it will be understood that shirt 400 may comprise other garments that may cover the thoracic or abdominal region of a patient, including sweaters, jackets, coats, etc., although in preferred embodiments a shirt that fits tightly to the patient's body is used to better retain the AP electromagnetic coils 420 in a more precise or controlled placement relative to the target tissue. AP electromagnetic coils 420 may be adapted for location or placement on the inside, outside or in a pocket of shirt 400, and may be integrated into or removably coupled thereto.

One or more cables or wires 450 may be provided to couple each of the coils 420 to an electronics box 460, which may house the remaining components of the MFT therapy system 100 of FIG. 1 such as APMFG 110, controller 130, power supply 150, and in some embodiments interface 140. In alternative embodiments, one or more of the APMFG 110, controller 130, power supply 150, or interface 140 may be provided separately from the electronics box 460. For example, a separate interface 140 may be provided as a mobile phone app that communicates with one or more of APMFG 110, controller 130, power supply 150, etc. Such an app-based interface may also provide information on the treatment therapy to the patient or a healthcare provider (e.g., displaying how long the therapy has been applied, whether a magnetic field is currently being applied to the target tissue from each of the coils 420, the frequency and/or field strength of the currently-provided magnetic fields, remaining battery life, etc.).

Figure 5:
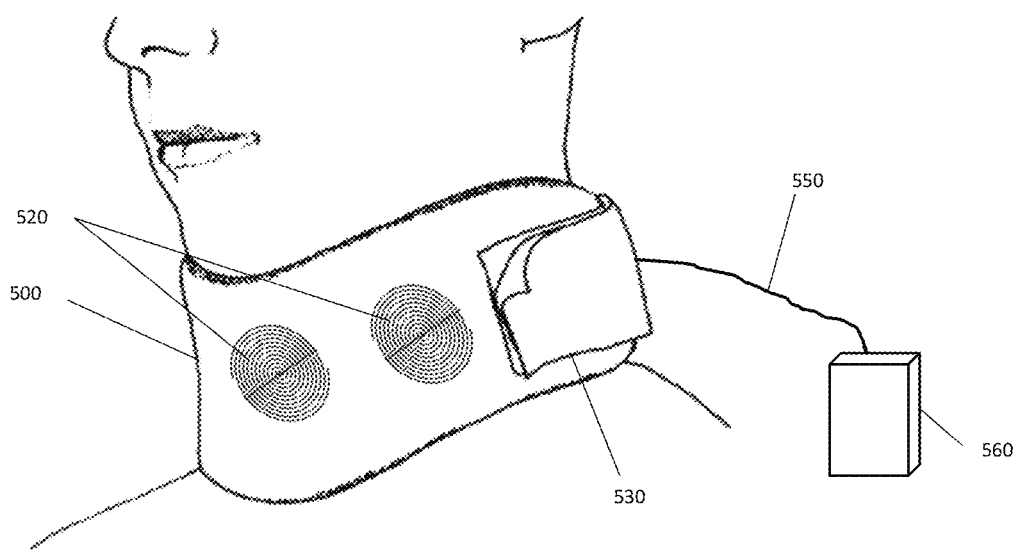
FIG. 5 is a front view of a retaining element comprising a neck cuff or collar having one or more AP electromagnetic coils for providing an AP magnetic field to a target area of a patient's body, according to one embodiment of the invention.

FIG. 5 illustrates a neck cuff or collar 500 that acts as a retaining element for one or more AP electromagnetic coils 520 for applying one or more magnetic fields to the treatment of cancer or other rapidly-dividing cells in a target tissue in a patient's neck area, including without limitation esophageal cancer, laryngeal cancer, etc. AP electromagnetic coils 520 may be similar to coils 120 described in FIG. 1, but may be adapted for placement in neck cuff or collar 500 based on the target treatment area or tissue. This may include changes in the size, geometry, or other characteristics to enable effective placement in neck cuff 500 and for treatment of the particular target tissue. Neck cuff or collar 500 preferably includes a securing and/or adjustment tab 530 (e.g., Velcro) to adjust the cuff or collar to the patient's size and to secure it in a fixed position relative to the patient's neck. In one alternative embodiment, a neck scarf may be used as a retaining element. AP electromagnetic coils 520 may be adapted for location or placement on the inside, outside or in a pocket of neck cuff or collar 500, and may be integrated into or removably coupled thereto.

One or more cables or wires 550 may be provided to couple each of the coils 520 to an electronics box 560, which may house the remaining components of the MFT therapy system 100 of FIG. 1 such as APMFG 110, controller 130, power supply 150, and in some embodiments interface 140. In alternative embodiments, one or more of the APMFG 110, controller 130, power supply 150, or interface 140 may be provided separately from the electronics box 560. For example, a separate interface may be provided as a mobile phone app that communicates with one or more of APMFG 110, controller 130, power supply 150, etc. Such an app-based interface may also provide information on the treatment therapy to the patient or a healthcare provider (e.g., displaying how long the therapy has been applied, whether a magnetic field is currently being applied to the target tissue from each of the coils 520, the frequency and/or field strength of the currently-provided magnetic fields, remaining battery life, etc.).

Figure 6:
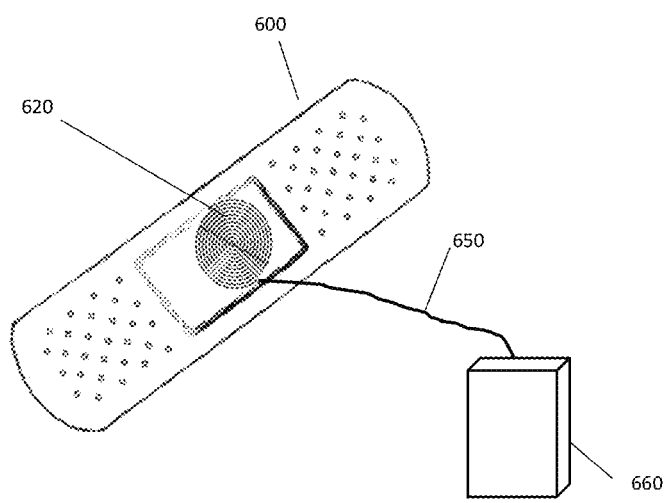
FIG. 6 is a front view of a retaining element comprising a bandage having one or more AP electromagnetic coils for providing an AP magnetic field to a target area of a patient's body, according to one embodiment of the invention.

FIG. 6 illustrates a bandage 600 that acts as a retaining element for one or more magnetic coils 620 for applying one or more magnetic fields to the treatment of cancer or other rapidly-dividing cells in a target tissue anywhere on the body. Magnetic coils 620 may be similar to those described in FIG. 1, but may be adapted for placement in bandage 600 based on the target tissue. This may include changes in the size, geometry, or other characteristics to enable effective placement in bandage 600 and for treatment of any of a variety of different target tissues. Magnetic coils 620 may be adapted for location or placement on the inside, outside or in a pocket of bandage 600, and may be integrated into or removably coupled thereto.

One or more cables or wires 650 may be provided to couple each of the coils 620 to an electronics box 660, which may house the remaining components of the MFT therapy system 100 of FIG. 1 such as APMFG 110, controller 130, power supply 150, and in some embodiments interface 140. In alternative embodiments, one or more of the APMFG 110, controller 130, power supply 150, or interface 140 may be provided separately from the electronics box 560. For example, a separate interface may be provided as a mobile phone app that communicates with one or more of APMFG 110, controller 130, power supply 150, etc. Such an app-based interface may also provide information on the treatment therapy to the patient or a healthcare provider (e.g., displaying how long the therapy has been applied, whether a magnetic field is currently being applied to the target tissue from each of the coils 620, the frequency and/or field strength of the currently-provided magnetic fields, remaining battery life, etc.).

Certain embodiments of the retaining element may also provide additional features to enable the MFT therapy to be conveniently delivered to the target body area or tissue. In one embodiment, the retaining element may have integrated magnetic coils 120, APMFG 110, and controller 130, either as separate items in the retaining element or as a single unit. A wire (not shown) may be provided to couple the power supply to one or more of the APMFG 110, coils 120, controller 130, and interface 140. In one embodiment, the power supply 150 provides power to the controller, which includes circuitry (e.g., rectifiers, converters, transformers, etc.) to modify the electrical power received from the power supply to provide electrical power to controller 130, which in turn distributes power to the APMFG 110, AP electromagnetic coils 120, and interface 140. In this embodiment, a power supply (e.g., a battery) may be located elsewhere in close proximity to the patient (e.g., in a pocket in the patient's trousers or a jacket).

In some embodiments, the MFT therapy may be provided to a patient in combination with one or more other therapies such as an anti-cancer drug, radiation therapy, or TTF therapy (e.g., therapy as described in U.S. Pat. Nos. 6,868,289 or 8,019,414). The MFT therapy system 100 preferably permits the other (i.e., non-MFT) therapy to be provided at a lower dosage than would be administered in the absence of the MFT therapy to the target body area or tissue, or at a reduced frequency than would be administered in the absence of the MFT therapy, or both. In various embodiments, the co-therapy applied with the MFT therapy may be a drug selected from a chemotherapy drug, a hormone receptor drug, targeted therapy drugs, immunotherapy, angiogenesis inhibitor drugs, a checkpoint inhibitor drug, and a HER2 receptor drug. In other embodiments the co-therapy may be a radiation therapy selected from an internal radiation therapy and an external beam radiation therapy. In still other embodiments, the co-therapy applied with the MFT therapy may be a TTF therapy involving the application of electrical fields to the target tissue. Without being bound by theory, it is anticipated that one or more co-therapies (or adjuvant therapies), when combined with MFT therapy, may achieve superior results than either therapy when administered alone. In various embodiments, the combination therapy may comprise administering MFT therapy with an anti-cancer drug, radiation, or TTF therapy either simultaneously or sequentially.

It may be desirable in some instances to shield non-target body areas from the MFT therapy fields. In such instances an optional magnetic field shield (not shown) may be provided to shield the non-target areas from the effects of the magnetic fields. In some embodiments, highly localized shields may be provided to shield specific structures within the target body area of the patient, such as specific blood vessels or organ structures that are adjacent to the target rapidly-dividing cells.

It is known that electric fields induce magnetic fields and vice versa. However, without being bound by theory, the present invention involving MFT therapy appears to provide a therapy having a different mode of action than prior art TTF and/or drug therapies. In particular, TTF therapies use capacitive electrodes to induce primarily electric fields at relatively high electric field strengths. According to reported literature (e.g., Kirson et al., Cancer Research 2004) TTF therapies begin to inhibit tumor cell growth at a field strength of about 100 V/m at frequencies of 50-250 kHz. In one recent experiment (see Experiment 1 below), MFT therapies showed surprising results with a similar inhibition of tumor cell growth as reported for TTF therapies but at a fraction (e.g., less than 3%) of typical TTF therapy electric field strengths.

Experiment 1

Figure 7A:
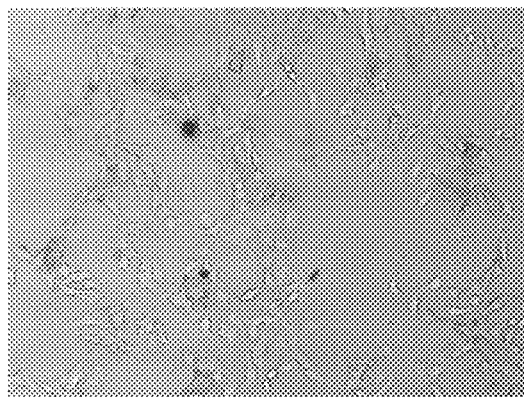
FIG. 7A is a photograph at 10× magnification of untreated B16F10 mouse melanoma cells incubated for 24 hours.
Figure 7B:
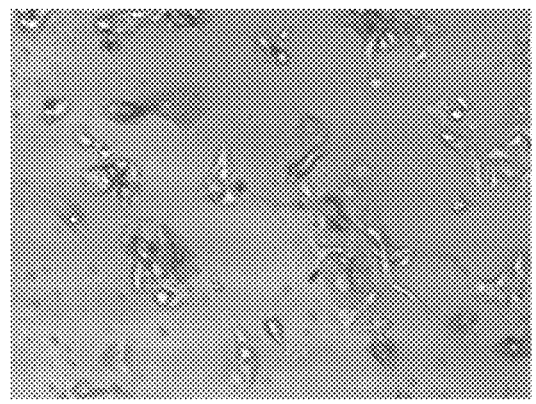
FIG. 7B is a photograph of B16F10 mouse melanoma cells exposed to an AP magnetic field for 24 hours according to one embodiment of the invention.

Mouse melanoma cells (B16F10 cell line, obtained from the University of California-Berkeley) were incubated in Dulbecco's Modified Eagle Medium (DMEM) in 36 middle wells (5.0 mm diameter) of a 96 well plate for 24 hours at 37° C. The cells in each of the 36 treatment wells were then exposed for 24 hours to an alternating magnetic field at a frequency of 150 kHz and a magnetic field strength of approximately 0.8 mT using a Helmholtz coil, maintained at a temperature of 37° C. Control wells were not exposed to the alternating magnetic field and were incubated at 37° C. for the same time period. After 24 hours, the alternating magnetic field was discontinued and histology was performed for cells in each well (both treatment and control). FIGS. 7A and 7B are illustrative of the differences between typical control and treatment wells. Controls exhibited a significantly higher cell count per well as shown by gross comparison. In addition, control cells maintained a typically angular morphological structure as indicating in FIG. 7A. Magnetic field-treated cells showed significantly decreased cell count and in addition demonstrated rounded morphology indicating cell stress, as shown in FIG. 7B.

Figure 8:
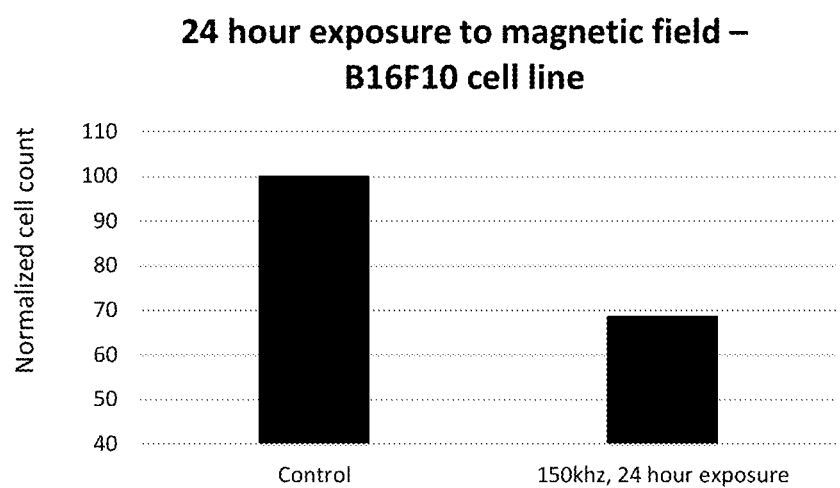
FIG. 8 is a bar graph showing the reduction in cell counts of B16F10 mouse melanoma cells treated with an AP magnetic field for 24 hours compared to untreated controls.

FIG. 8 provides a bar chart comparison summarizing the results of treatments performed on two different plates with 36 wells in each plate. Normalizing the cell counts of the control wells as 100, the treated cells showed a reduction of approximately 31%. Although treatment by magnetic fields and electrical fields (e.g., TTF therapy) are fundamentally different (e.g., using coils vs electrodes and generating primarily magnetic vs. electric fields), it is possible to calculate the strength of the induced electric field from the coils used in Experiment 1 using the equation $$E_{nc} = \frac{r}{2} \frac{dB}{dt}$$

Using equation 1 yields a maximum inducted voltage of 2.34 V/m, or less than 3% of the electric field strengths reported as required for inhibitory activity in TTF therapy. Because Experiment 1 indicates that MFT therapy exhibits effects on cancer cells at such a small fraction of the electrical field strength of TTF therapy, it enables therapies having significant advantages over TTF therapies, including without limitation ambulatory therapies that allow patients to continue many ordinary day-to-day activities without interruption, and minimal encumbrance or burden.

Part of the advantage of MFT therapies over TTF therapies stems from the different hardware configurations of the two systems. While TTF therapies use insulated (e.g., ceramic coated) electrodes, the use of coils instead of electrodes in MFT therapy confers a number of benefits. Because MFT therapy coils—in contrast to the insulated electrodes of TTF therapies—do not need to be in direct contact with the body, MFT coils can be separated from target issue by one or more clothing layers (e.g., a garment or undergarment). By applying magnetic fields through clothing, MFT therapies provide increased patient comfort and a less cumbersome patient experience.

In addition, MFT therapies can be implemented with significantly less risk to the patient than TTF therapies involving electrodes. The use of coils instead of electrodes results in only a de minimis induced electrical current during MFT therapies, and thus the risk of electrical shorting and consequent uncontrolled heating of patient body tissue is negligible.

Furthermore, because MFT therapies involve coils that can be made relatively small and with no current flow through the patient's body, systems for MFT therapies can allow long treatment periods to target cancer and other hyperproliferating cells with little inconvenience to the patient. These and other advantages of MFT therapies over TTF therapies will be more fully appreciated by persons of skill in the art in view of the present disclosure.

In various embodiments, the present invention relates to the subject matter of the following numbered paragraphs.

101. A method of treating cancer cells in a target body area of a patient, comprising:
coupling an AP electromagnetic coil to the target body area; and
applying an alternating polarity (AP) magnetic field to the target body area using the AP electromagnetic coil, the AP magnetic field having a frequency of 0.5-500 kHz and a field strength of 0.05-5 mT, wherein the AP magnetic field selectively affects the cancer cells to achieve at least one of damaging the cancer cells, inhibiting the growth of the cancer cells, reducing tumor size, inhibiting angiogenesis, or preventing metastasis of the cancer cells, while leaving non-cancer cells substantially unharmed.

102. The method of numbered paragraph 101, further comprising:
coupling a controller to the AP electromagnetic coil, wherein the controller controls the frequency and field strength of the AP magnetic field.

103. The method of claim numbered paragraph 101, wherein applying an AP magnetic field comprises applying an AP magnetic field having a frequency of 25-400 kHz and a field strength of 0.2-2 mT.

104. The method of claim numbered paragraph 101, wherein applying an AP magnetic field comprises applying an AP magnetic field having a frequency of 100-300 kHz and a field strength of 0.5-1.2 mT.

201. A method of treating cancer cells in a target body area of a patient, comprising:
providing at least one electromagnetic coil;
providing a controller coupled to the at least one electromagnetic coil;
coupling the at least one electromagnetic coil to the target body area;
applying to the target body area an alternating polarity (AP) magnetic field having a frequency of 0.5-500 kHz and a field strength of 0.05-5 mT, wherein the AP magnetic field is generated by the at least one electromagnetic coil under the control of the controller, and the AP magnetic field selectively affects the cancer cells to achieve at least one of damaging the cancer cells, inhibiting the growth of the cancer cells, reducing tumor size, inhibiting angiogenesis, or preventing metastasis of the cancer cells, while leaving non-cancer cells substantially unharmed.

202. The method of numbered paragraph 201, wherein applying an AP magnetic field comprises applying an AP magnetic field having a frequency of 25-400 kHz and a field strength of 0.2-2 mT.

203. The method of numbered paragraph 201, wherein applying an AP magnetic field comprises applying an AP magnetic field having a frequency of 100-300 kHz and a field strength of 0.5-1.2 mT.

204. The method of numbered paragraph 201, wherein applying an AP magnetic field comprises applying the AP electrical field to the target body area according to at least one of a treatment duty cycle and a field strength duty cycle.

205. The method of numbered paragraph 204, wherein the treatment duty cycle comprises alternating periods of an on-time in which the AP magnetic field is applied to the target tissue, and an off-time in which the AP magnetic field is not applied to the target tissue.

206. The method of numbered paragraph 204, wherein the field strength duty cycle comprises alternating periods in which the AP magnetic field is applied to the target tissue for a first time period at a first field strength followed by a second time period at a second field strength.

207. The method of numbered paragraph 201, wherein the AP magnetic field comprises a bimodal magnetic field frequency distribution comprising a first variable AP magnetic field that varies the magnetic field frequency between a first lower limit and a first upper limit and a second variable AP magnetic field that varies the magnetic field frequency between a second lower limit and a second upper limit.

208. The method of numbered paragraph 201, wherein the AP magnetic field comprises at least one of a variable frequency and a variable field strength.

209. The method of numbered paragraph 201, further comprising administering to the patient at least one additional anti-cancer therapy selected from an anti-cancer drug, a radiation therapy, and TTF therapy.

210. The method of numbered paragraph 209, wherein administering a TTF therapy comprises applying at least one AC electrical field to the target tissue, wherein the AC electrical field comprises a frequency of 50-500 kHz and an electric field strength of about 10-1000 V/m.

301. A system for treating cancer cells in a target body area of a patient comprising:
at least one electromagnetic coil coupled to a target body area; and
a controller for controlling the at least one electromagnetic coil to generate and apply to the target body area an AP magnetic field having a frequency of 0.5-500 kHz and a field strength of 0.05-5 mT, wherein the AP magnetic field selectively affects the cancer cells to achieve at least one of damaging the cancer cells, inhibiting the growth of the cancer cells, reducing tumor size, inhibiting angiogenesis, or preventing metastasis of the cancer cells, while leaving non-cancer cells substantially unharmed.

302. The system of numbered paragraph 301, wherein the cancer cells are one of breast cancer cells, lung cancer cells, lung carcinoid tumor cells, thymic cancer cells, tracheal cancer cells, pancreatic cancer cells, liver cancer cells, stomach cancer cells, kidney cancer cells, ovarian cancer cells, colon cancer cells, rectal cancer cells, prostate cancer cells, throat cancer cells, thyroid cancer cells, mouth cancer cells, nose cancer cells, and salivary gland cancer cells.

303. The system of numbered paragraph 302 wherein the at least one electromagnetic coil is coupled to the target body area by a retaining element during the application of the AP magnetic field to the target body area.

304. The system of numbered paragraph 303, wherein the cancer cells are breast cancer cells, and the retaining element is a wearable garment selected from a bra, a shirt, and a vest.

305. The system of numbered paragraph 303, wherein the cancer cells are selected from lung cancer, lung carcinoid tumors, thymic malignancies, tracheal tumors, pancreatic cancer, liver cancer, stomach cancer, kidney cancer, ovarian cancer, colon cancer and rectal cancer, and the retaining element is a wearable garment selected from a bra, a shirt, a vest, and a jacket.

306. The system of numbered paragraph 303, wherein the cancer cells are lower-body cancer cells selected from prostate cancer cells, ovarian cancer cells, colon cancer cells, and rectal cancer cells, and the retaining element is an undergarment.

308. The system of numbered paragraph 301 wherein the at least one electromagnetic coil is coupled to the target body area by a retaining element during the application of the AP magnetic field to the target body area.

309. The system of numbered paragraph 308 wherein the retaining element is selected from a bra, a shirt, a vest, a jacket, an undergarment, and a bandage.

310. The system of numbered paragraph 301, wherein the at least one electromagnetic coil comprises a plurality of electromagnetic coils coupled to the target body area to obtain a desired magnetic field distribution in the target body area.

311. The system of numbered paragraph 301, further comprising:
an electromagnetic shield for shielding at least one non-target body area of the patient's body from exposure to the AP magnetic field.

401. A system for treating cancer cells in a target area of a patient's body comprising:
at least one electromagnetic coil coupled to a target body area; and
a controller for controlling the at least one electromagnetic coil to generate and apply to the target body area an alternating polarity (AP) magnetic field having a frequency of 5 Hz-500 kHz and a field strength of 0.05-5 mT, wherein the AP magnetic field selectively affects the cancer cells to achieve at least one of damaging the cancer cells, inhibiting the growth of the cancer cells, reducing tumor size, inhibiting angiogenesis, or preventing metastasis of the cancer cells, while leaving non-cancer cells substantially unharmed.

402. The system of numbered paragraph 401, further comprising: a power supply for supplying power to said electromagnetic coil.

The particular embodiments disclosed above are illustrative only, as the invention may be modified and practiced in different but equivalent manners apparent to those skilled in the art having the benefit of the teachings herein. Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept, spirit and scope of the invention. Examples are all intended to be non-limiting. It is therefore evident that the particular embodiments disclosed above may be altered or modified and all such variations are considered within the scope and spirit of the invention, which are limited only by the scope of the claims.

The invention claimed is:

1. A method of treating cancer cells in a target body area of a patient, comprising:
providing a magnetic field therapy system comprising:
an alternating polarity (AP) magnetic field generator;
one or more AP electromagnetic coils coupled to the AP magnetic field generator, wherein the one or more AP electromagnetic coils are energized by an electrical signal from the AP magnetic field generator to generate an AP magnetic field having at least a first frequency and a first field strength; and
a controller to control at least one of the first frequency and the first field strength of the AP magnetic field generated by the one or more AP electromagnetic coils;
coupling the one or more AP electromagnetic coils to the target body area;
generating an AP magnetic field having a first frequency of 0.5-400 kHz and a first field strength of 0.2-5 mT using the one or more AP electromagnetic coils;
applying the generated AP magnetic field to the target body area using the one or more AP electromagnetic coils, wherein the AP magnetic field selectively affects the cancer cells to prevent metastasis of the cancer cells, while leaving non-cancer cells substantially unharmed; and
treating the patient during at least a portion of the step of applying the generated AP magnetic field to the target body area with a chemotherapy drug.

2. The method of claim 1, wherein coupling the one or more AP electromagnetic coils to the target body area comprises using a retaining element to maintain the one or more AP electromagnetic coils in close proximity to the target body area, and wherein the retaining element is selected from a garment and a bandage.

3. The method of claim 2, wherein the cancer cells comprise at least one of:
brain cancer, and the retaining element is a hat;
breast cancer, and the retaining element is a wearable garment selected from a bra, a shirt, or a vest;
lung cancer, lung carcinoid tumors, thymic malignancies, tracheal tumors, pancreatic cancer, liver cancer, stomach cancer, kidney cancer, ovarian cancer, colon cancer and rectal cancer, and the retaining element is a wearable garment selected from a bra, a shirt, a vest, and a jacket;
a lower-body cancer selected from prostate cancer, ovarian cancer, colon cancer, and rectal cancer, and the retaining element is an undergarment;
skin cancer, and the retaining element is one of an adhesive bandage and a non-adhesive bandage; and
one of a throat, thyroid, mouth, nose, and salivary gland cancer, and the retaining element is selected from a neck cuff, a neck collar, and a scarf.

4. The method of claim 1, further comprising:
administering to the patient at least one additional anti-cancer therapy selected from a radiation therapy, an immunotherapy, a hormone therapy drug, a targeted therapy drug, an angiogenesis inhibitor drug, and tumor treatment field therapy.

5. The method of claim 4, wherein treating the patient with a chemotherapy drug and administering to the patient at least one additional anti-cancer therapy comprises treating the patient with a chemotherapy drug and administering the at least one additional anti-cancer therapy at one or more of:

a lower dosage than a dosage that would be administered in the absence of applying the generated AP magnetic field to the target body area; and a reduced dosing frequency compared to the frequency at which the chemotherapy drug and the at least one additional anti-cancer therapy would be administered in the absence of applying the generated AP magnetic field to the target body area.

6. The method of claim 1, wherein applying the AP magnetic field reduces a side effect of the chemotherapy drug.

7. The method of claim 1 wherein coupling the one or more AP electromagnetic coils to the target body area comprises coupling a plurality of AP electromagnetic coils to the target body area, wherein each coil in said plurality of coils is oriented so as to apply a desired AP magnetic field distribution in the target body area.

8. The method of claim 1, wherein coupling the one or more AP electromagnetic coils to the target body area comprises coupling a plurality of AP electromagnetic coils to the target body area, the method further comprising:
   selecting one or more coils from the plurality of coils to activate to apply the AP magnetic field based on one of
   1) the result of an imaging procedure selected from an MRI scan, a CT scan, a PET scan, and an X-ray, and
   2) a pathological analysis of the cancer cells selected from a microscopic analysis of a cell biopsy and a chemical test performed on the cancer cells;
and wherein applying the generated AP magnetic field to the target body area comprises applying the generated AP magnetic field to the target body area using the selected one or more AP electromagnetic coils.

9. The method of claim 1, wherein generating an AP magnetic field comprises one or more of:
   generating an AP magnetic field continuously for a first treatment period;
   generating an AP magnetic field intermittently for a second treatment period in alternating on-time periods, followed by off time periods in which an AP magnetic field is not generated;
   generating an AP magnetic field intermittently for one or more circadian treatment periods based on circadian rhythms of the patient; and
   generating an AP magnetic field intermittently for one or more third treatment periods at defined times of day.

10. The method of claim 1, wherein generating an AP magnetic field comprises one or more of:
   generating an AP magnetic field having a single first frequency of 0.5-400 kHz;
   generating an AP magnetic field for a defined time period having a first frequency of 0.5-400 kHz that varies in a defined pattern;
   generating an AP magnetic field having multiple simultaneous frequencies of 0.5-400 kHz.

11. The method of claim 10, wherein generating an AP magnetic field for a defined time period having a first frequency of 0.5-400 kHz that varies in a defined pattern comprises at least one of:
   generating an AP magnetic field in which the first frequency changes randomly at a defined rate;
   generating an AP magnetic field in which the first frequency varies in a Gaussian distribution in one or more sub-ranges within the range of 0.5-400 kHz;
   generating an AP magnetic field in which the first frequency varies in a non-Gaussian distribution in one or more sub-ranges within the range of 0.5-400 kHz.

12. The method of claim 1, wherein applying the generated AP magnetic field to the target body area is performed one of:
   prior to a surgical procedure to treat the patient;
   during a surgical procedure to treat the patient;
   after a surgical procedure to treat the patient;
   prior to a radiation procedure to treat the patient;
   during a radiation procedure to treat the patient; and
   after a radiation procedure to treat the patient.

13. The method of claim 1, wherein generating an AP magnetic field comprises generating an AP magnetic field having a first frequency within the range of 25-400 kHz.

14. The method of claim 1, wherein generating an AP magnetic field comprises generating an AP magnetic field having a first frequency within the range of 50-300 kHz and a first field strength within the range of 0.2-2 mT.

15. The method of claim 1, wherein generating an AP magnetic field comprises generating an AP magnetic field having a first frequency within the range of 0.5-250 kHz and a first field strength within the range of 0.2-2 mT.

16. The method of claim 1, wherein generating an AP magnetic field comprises generating an AP magnetic field having a first frequency within the range of 0.5-150 kHz and a first field strength within the range of 0.2-2 mT.

17. The method of claim 1, wherein treating the patient with a chemotherapy drug comprises administering the chemotherapy drug at one or more of:
   a lower dosage than a dosage that would be administered in the absence of applying the generated AP magnetic field to the target body area; and
   a reduced dosing frequency compared to the frequency at which the chemotherapy drug would be administered in the absence of applying the generated AP magnetic field to the target body area.

18. The method of claim 1, wherein generating an AP magnetic field comprises generating an AP magnetic field in a burst mode defined by alternating on-time and off-time periods repeated at a second frequency, wherein each of the on-time periods of the second frequency comprises an AP magnetic field having the first frequency of 0.5-400 kHz.

19. The method of claim 1, wherein generating an AP magnetic field comprises generating an AP magnetic field having a first waveform, the method further comprising:
   performing amplitude modulation of the first waveform of the generated AP magnetic field prior to the step of applying the generated AP magnetic field to the target body area.

20. A method of treating cancer cells in a target body area of a patient, comprising:
   providing a magnetic field therapy system comprising:
      an alternating polarity (AP) magnetic field generator;
      one or more AP electromagnetic coils coupled to the AP magnetic field generator, wherein the one or more AP electromagnetic coils are energized by an electrical signal from the AP magnetic field generator to generate an AP magnetic field having at least a first frequency and a first field strength; and
      a controller to control at least one of the first frequency and the first field strength of the AP magnetic field generated by the one or more AP electromagnetic coils;
   coupling the one or more AP electromagnetic coils to the target body area;
   generating an AP magnetic field having a first frequency of 0.5-400 kHz and a first field strength of 0.2-5 mT using the one or more AP electromagnetic coils;

applying the generated AP magnetic field to the target body area using the one or more AP electromagnetic coils, wherein the AP magnetic field selectively affects the cancer cells to prevent metastasis of the cancer cells, while leaving non-cancer cells substantially unharmed; and treating the patient during at least a portion of the step of applying the generated AP magnetic field to the target body area with at least one of an immunotherapy drug, a chemotherapy drug, a radiation therapy, a hormone therapy drug, a targeted therapy drug, an angiogenesis inhibitor drug, and tumor treatment field therapy.

\* \* \* \* \*